US009408395B2

(12) United States Patent
Castillo et al.

(10) Patent No.: US 9,408,395 B2
(45) Date of Patent: Aug. 9, 2016

(54) **PROCESS FOR POTENTIATING THE PRODUCTION OF LINGZHI MUSHROOM (*GANODERMA LUCIDUM*) SUBSTANCES AND ANTIFUNGAL ACTIVITY THEREOF**

(71) Applicants: UNIVERSIDAD DE ANTIOQUIA (UDEA), Medellín (CO); ASOCIACIÓN DE BANANEROS DE COLOMBIA (AUGURA), Medellín (CO)

(72) Inventors: John Jairo Mira Castillo, Medellín (CO); Paola Andrea Zapata Ocampo, Medellín (CO); Lucía Atehortúa Garcés, Medellín (CO); Liuda Johana Sepúlveda Arango, Medellín (CO); Diego Fernando Rojas Vahos, Medellín (CO)

(73) Assignee: Universidad De Antioquia, Medellin (CO)

( * ) Notice: Subject to any disclaimer, the term of this patent is extended or adjusted under 35 U.S.C. 154(b) by 0 days.

(21) Appl. No.: 13/921,031

(22) Filed: Jun. 18, 2013

(65) Prior Publication Data

US 2014/0242036 A1 Aug. 28, 2014

(30) Foreign Application Priority Data

Feb. 22, 2013 (CO) .................................. 13-036699

(51) Int. Cl.

| | |
|---|---|
| ***A01N 63/04*** | (2006.01) |
| ***A01N 65/00*** | (2009.01) |
| ***C07K 14/375*** | (2006.01) |
| ***C12N 1/06*** | (2006.01) |
| ***C12P 1/02*** | (2006.01) |
| ***C12N 1/14*** | (2006.01) |
| ***C12N 13/00*** | (2006.01) |
| *C12P 21/00* | (2006.01) |
| *C12P 33/00* | (2006.01) |
| *C12P 7/64* | (2006.01) |

(52) U.S. Cl.

CPC ................ *A01N 65/00* (2013.01); *A01N 63/04* (2013.01); *C07K 14/375* (2013.01); *C12N 1/06* (2013.01); *C12N 1/14* (2013.01); *C12N 13/00* (2013.01); *C12P 1/02* (2013.01); *C12P 7/6436* (2013.01); *C12P 21/00* (2013.01); *C12P 33/00* (2013.01)

(58) Field of Classification Search

None

See application file for complete search history.

(56) References Cited

U.S. PATENT DOCUMENTS

2008/0138875 A1 6/2008 Atehortua

OTHER PUBLICATIONS

Wang et al., Appli. Microbiol. Biotechnol., 2006, vol. 72, p. 508-513.*

Wang & Ng et al., Peptides 2006, vol. 27, p. 27-30.*

Nematpour et al., Journal of Biological Sciences, 2008, vol. 8, No. 3, p. 526-533.*

Electrical field effect on mycelium biomass production of the medicinal fungus *Ganoderma lucidum* (Actual Biol 2010, 32 (92): p. 5-17).

Bajorath, J., Hinrichs, W., and Saenger, W. (1988) The enzymatic activity of proteinase K is controlled by calcium., The Federation of European Biochemical Societies Journal 176, 441-447.

Phansri, K., Sarnthima, R., Thammasirirak, S., Boonchalee, P., and Khammuang, S. (2011) Antibacterial Activity of *Bauhinia acuminata* L. Seed Protein Extract with Low Hemolytic Activity Against Human Erythrocytes, Chiang Mai Journal of Science 38, 242-251.

Bradford, M. M. (1976) A rapid and sensitive method for the quantitation of microgram quantities of protein utilizing the principle of protein-dye binding., Analytical biochemistry 72, 248-54.

Rodríguez, A. (2010) Caracterización de proteínas con actividad antifúungica producidas por Penicillium chrysogenum, Planta, Universidad de Extremadura.

Espinel-Ingroff, A., Canton, E., and Peman, J. (2009) Updates in antifungal susceptibility testing of filamentous fungi, Current Fungal Infection Reports 3, 133-141.

Liu, M., Seidel, V., Katerere, D. R., and Gray, A. I. (2007) Colorimetric broth microdilution method for the antifungal screening of plant extracts against yeasts., Methods 42, 325-329.

Mesa, A. M., Saez, J., Blair Trujillo, S., and Arango, E. (2007) Actividad antiplasmodial de extractos de la planta Calophyllum lucidum, Scientia et Technica Año 13, 217-219.

Hall, G., and Parshall, S. (2002) Use of the concentration gradient diffusion assay (Etest) for suceptibility testing of anaerobes, fungi, and *Mycobacterium* spp., Clinical Microbiology Newsletter 24, 105-109.

Wasser, S. P. (2002) Medicinal mushrooms as a source of antitumor and immunomodulating polysaccharides., Applied microbiology and biotechnology 60, 258-74.

Asatiani, M., Kachlishvili, E., Khardziani, T., Metreveli, E., Mikiashvili, N., Songulashvili, G., Tsiklauri, N., Wasser, S., and Elisashvili, V. (2008) Basidiomycetes as a source of antioxidants, lectins, polysaccharides, and enzymes, Journal of Biotechnology 136, 7-17.

Akavia, E., Beharav, a, Wasser, S. P., and Nevo, E. (2009) Disposal of agro-industrial by-products by organic cultivation of the culinary and medicinal mushroom *Hypsizygus marmoreus*., Waste management (New York, N.Y.), Elsevier Ltd 29, 1622-7.

(Continued)

*Primary Examiner* — Kade Ariani

(74) *Attorney, Agent, or Firm* — Boulware & Valoir

(57) ABSTRACT

The instant invention refers to a novel process for potentiating the production of substances with antifungal activity obtained from *Ganoderma lucidum*, using a technological device for the differential, qualitative and quantitative expression of proteins and other bioactive molecules, selected from the group consisting of polysaccharides, triterpenoids, fatty acids and ganoderic acids. The compositions containing said substances showed antifungal activity and mycelium growth and fungi ascospore germination inhibiting activity, amongst them *Mycosphaerella fijiensis*, primary pathogenic agent causing black Sigatoka disease in banana and plantain crop fields.

8 Claims, 6 Drawing Sheets

(56) References Cited

OTHER PUBLICATIONS

Lewinsohn, D., Nevo, E., Hadar, Y., Wasser, S., and Beharav, A. (2000) Ecogeographical variation in the Pleurotus eryngii complex in Israel, Mycological Research 104, 1184-1190.
Wang, H., and Ng, T. B. (2006) Ganodermin, an antifungal protein from fruiting bodies of the medicinal mushroom *Ganoderma lucidum*., Peptides 27, 27-30.
Xu, X., Yan, H., Chen, J., and Zhang, X. (2011) Bioactive proteins from mushrooms., Biotechnology advances, Elsevier Inc. 29, 667-74.
Churchill, A. C. L. (2011) *Mycosphaerella fijiensis*, the black leaf streak pathogen of banana: progress towards understanding pathogen biology and detection, disease development, and the challenges of control., Molecular Plant Pathology, Wiley Online Library 12, 307-328.
Leskosek-Cukalovic, I., Despotovic, S., Lakic, N., Niksic, M., Nedovic, V., and Tesevic, V. (2010) *Ganoderma lucidum*—Medical mushroom as a raw material for beer with enhanced functional properties, Food Research International 43, 2262-2269.
Zapata, P., Rojas, D., and Atehortua, L. (2012) Production of biomass, polysaccharides and ganoderic acid using non-conventional carbon sources under submerged culture of the Ganoderma lucidum, International Journal of Medicinal Mushrooms in press.
Zapata, P., Rojas, D., Ramirez, D., Fernandez, C., and Atehortua, L. (2009) Effect of Different Light-Emitting Diodes on Mycelial Biomass Production of Ling Zhi or Reishi Medicinal Mushroom *Ganoderma lucidum* (W. Curt.: Fr.) P. Karst. (Aphyllophoromycetideae), International Journal of Medicinal Mushrooms 11, 93-99.
Panchaud, A., Affolter, M., and Kussmann, M. (2012) Mass spectrometry for nutritional peptidomics: How to analyze food bioactives and their health effects., Journal of proteomics, Elsevier B.V. 75, 3546-3559.
Jiang, L., He, L., and Fountoulakis, M. (2004) Comparison of protein precipitation methods for sample preparation prior to proteomic analysis, Journal of Chromatography A 1023, 317-320.
Harder, A. (2008) Sample preparation procedure for cellular fungi, Methods in molecular biology 425, 265-273.
Dong, H., Kemptner, J., Marchetti-Deschmann, M., Kubicek, C. P., and Allmaier, G. (2009) Development of a MALDI two-layer volume sample preparation technique for analysis of colored conidia spores of Fusarium by MALDI linear TOF mass spectrometry., Analytical and bioanalytical chemistry 395, 1373-83.
Yin, Q. Y., De Groot, P. W. J., De Koster, C. G., and Klis, F. M. (2008) Mass spectrometry-based proteomics of fungal wall glycoproteins., Trends in microbiology 16, 20-6.
Lau, B. F., Aminudin, N., and Abdullah, N. (2011) Comparative SELDI-TOF-MS profiling of low-molecular-mass proteins from Lignosus rhinocerus (Cooke) Ryvarden grown under stirred and static conditions of liquid fermentation., Journal of microbiological methods, Elsevier B.V. 87, 56-63.
DuBois, M., Gilles, K. a., Hamilton, J. K., Rebers, P. a., and Smith, F. (1956) Colorimetric Method for Determination of Sugars and Related Substances, Analytical Chemistry 28, 350-356.
Stover, R. H. (1983) The effect of temperature on ascospore germ tube growth of *Mycosphaerella musicola* and *Mycosphaerella fijiensis* var. difformis, Fruits 38, 625-628.
Madrigal, R., Arroyo, T., Astua, T., and Monreri, S. (2012) List of Monitoring Methods, FRAC (Fungicide Resistance Action Committee) 1, 1-3.
McDonald, J. H. (2009) Handbook of Biological Statistics Second edi., pp. 127-202, Sparky House Publishing, Baltimore, Maryland, USA.
Ortiz, A., and Orduz, S. (2001) In vitro evaluation of Trichoderma and Gliocladium antagonism against the symbiotic fungus of the leaf-cutting ant *Atta cephalotes*, Mycopathologia 150, 53-60.
Viveros, J., and Costaño, J. (2006) Evaluación in vitro de extractos vegetales sobre Mycosphaerella fijiensis Morelet, In Vitro 14, 37-50.
Etebu, E., Pasberg-Gauhl, C., Gauhl, F., Ayibo, D., and Kalio, L. (2005) Efecto de la luz y aeracion sobre la esporulacion y crecimiento lineal de Mycosphaerella fijiensis, Infomusa 14, 24-25.
Jacome, L. H., and Schuh, W. (1993) Effect of Temperature on Growth and Conidial Production in-Vitro, and Comparison of Infection and Aggressiveness in-vivo among Isolates of Mycosphaerella-Fijiensis Var Difformis, Tropical Agriculture 70, 51-59.
Pineda, F., Uribe, S., Saldarriaga, Y., and Calle, J. (2003) Susceptibilidad de Rhodnius pallescens (Hemiptera: Reduviidae) de V estadio de desarrollo a la acción de *Beauveria* spp., Entomotrópica 18, 163-168.
Donini, L. P., Bernardi, E., and Do Nascimento, J. S. (2006) Desenvolvimento in vitro de Agaricus brasiliensis em meios suplementados com diferentes farelos, Pesquisa Agropecuária Brasileira 41, 995-999.
Elad, Y., and Kapat, A. (1999) The role of Trichoderma harzianum protease in the biocontrol of Botrytis cinerea, European Journal of Plant Pathology, Springer 105, 177-189.
Mazurkiewicz-Zapalowicz, K., and Kolodziejczyk, L. (2009) Antagonistic interactions between saprotrophic fungi and geohelminths. 1. Saprotrophic fungi in the biological control of phytopathogenic geohelminths, Wiadomosci Parazytologiczne 55, 1-8.
Reyes, Y., Martinez, B., and Infante, D. (2008) Evaluation of the antagonistic activity of thirteen *Trichoderma* spp ., Protección Vegetal 23, 112-117.
Viveros, J. (2001) In vitro evaluation of Trichoderma and Gliocladium antagonism against the symbiotic fungus of the leaf-cutting ant *Atta cephalotes*, Mycopathologia 150, 53-60.
Silva, A., Rodrigues, A., Bacci, M., Pagnocca, F. C., and Bueno, O. C. (2006) Susceptibility of the ant-cultivated fungus *Leucoagaricus gongylophorus* (Agaricales: Basidiomycota) towards microfungi., Mycopathologia 162, 115-119.
Ceballos, I. C. (2009) Selección de bacterias aeróbicas formadoras de endospora aisladas de la filosfera de cultivares de musa en el Urabá Antioqueño, con potencial antagónico contra Mycosphaerella fijiensis Morelet, Universidad Nacional Colombia.
Slifkin, M., Cumbie, R. (1988) Congo red as a fluorochrome for the rapid detection of fungi., Journal of Clinical Microbiology 26, 827-830.
Riveros, A. S., Giraldo, C. I., and Gamboa, A. (2003) Microbiological control of black leaf streak disease, Seven 287-296.
Jacome, L. H., Schuh, W., and Stevenson, R. E. (1991) Effect of Temperature and Relative Humidity on Germination and Germ Tube Development of *Mycosphaerella fijiensis* var. *difformis*, Phytopathology 81, 1480-1485.
Jacome, L., Lepoivre, P., Marin, D., Ortiz, R., Romero, R., and Escalant, J. V. (2002) Mycosphaerella leaf spot diseases of bananas•:present status and outlook, Network (Jacome, L., Lepoivre, P., Marin, D., Ortiz, R., Romero, R., and Escalant, J. V, Eds.) First edit., pp. 71-212, San Jose de Costa Rica.
Honma, Y., Nakabayashi, I., Tamaoki, D., Kasahara, H., Ishioka, N., Shimazu, T., Kasahara, H., Yamada, M., Karahara, I., and Kamisaka, S. (2003) Optical microscopy of Arabidopsis seedlings fixed in non-fresh FAA using Kennedy Fixation Tubes., Uchu Seibutsu Kagaku 17, 307-308.
Müller, W. H., Van Aelst, A. C., Humbel, B. M., Van Der Krift, T. P., and Boekhout, T. (2000) Field-emission scanning electron microscopy of the internal cellular organization of fungi., Scanning 22, 295-303.
Cao, R., Liu, X., Gao, K., Mendgen, K., Kang, Z., Gao, J., Dai, Y., and Wang, X. (2009) Mycoparasitism of endophytic fungi isolated from reed on soilborne phytopathogenic fungi and production of cell wall-degrading enzymes in vitro., Current Microbiology 59, 584-592.
Beveraggi, A., Mourichon, X., and Salle, G. (1995) Comparative-Study of the First Stages of Infection in Sensitive and Resistant Banana Plants with Cercospora-Fijiensis (Mycosphaerella-Fifiensis), Responsible for Black Leaf Streak Disease, Canadian Journal of Botany 73, 1328-1337.
Jing, H.-C., Lovell, D., Gutteridge, R., Jenk, D., Kornyukhin, D., Mitrofanova, O. P., Kema, G. H. J., and Hammond-Kosack, K. E.

(56) References Cited

OTHER PUBLICATIONS (2008) Phenotypic and genetic analysis of the Triticum monococcum-Mycosphaerella graminicola interaction., New Phytologist 179, 1121-1132.

Masaphy, S., Levanon, D., Tchelet, R., and Henis, Y. (1987) Scanning Electron Microscope Studies of Interactions between Agaricus bisporus (Lang) Sing Hyphae and Bacteria in Casing Soil, Applied and Environmental Microbiology 53, 1132-1137.

Inbar, J., and Chet, I. (1992) Biomimics of fungal cell-cell recognition by use of lectin-coated nylon fibers., Journal of Bacteriology 174, 1055-1059.

Campos Muñoz, A. (2010) Cell therapy with chondrocytes. Evaluation of cell viability in cultures, Anales de la Real Academia Nacional de Medicina 127, 269-281.

Semighini, C. P., and Harris, S. D. (2010) Methods to detect apoptotic-like cell death in filamentous fungi., Methods in Molecular Biology 638, 269-279.

Chung, W. T., Lee, S. H., Kim, J. D., Park, Y. S., Hwang, B., Lee, S. Y., and Lee, H. Y. (2001) Effect of mycelial culture broth of Ganoderma lucidum on the growth characteristics of human cell lines., Journal of bioscience and bioengineering 92, 550-555.

Campos Ziegenbein, F., Hanssen, H.-P., and König, W. A. (2006) Secondary metabolites from Ganoderma lucidum and Spongiporus leucomallellus., Phytochemistry 67, 202-211.

Jang, K.-J., Han, M.-H., Lee, B.-H., Kim, B.-W., Kim, C.-H., Yoon, H.-M., and Choi, Y.-H. (2010) Induction of apoptosis by ethanol extracts of Ganoderma lucidum in human gastric carcinoma cells., Journal of acupuncture and meridian studies, Korean Pharmacopuncture Institute 3, 24-31.

Shimizu, M., and Wariishi, H. (2005) Development of a sample preparation method for fungal proteomics., FEMS Microbiology Letters 247, 17-22.

Munoz, K., Bravo, K., Zapata, P., and Londono, J. (2007) Caracterización preliminar del enzima polifenol oxidasa en frutas tropicales: implicaciones en su proceso de industrialización, Scientia et Technica XIII, 161-164.

* cited by examiner

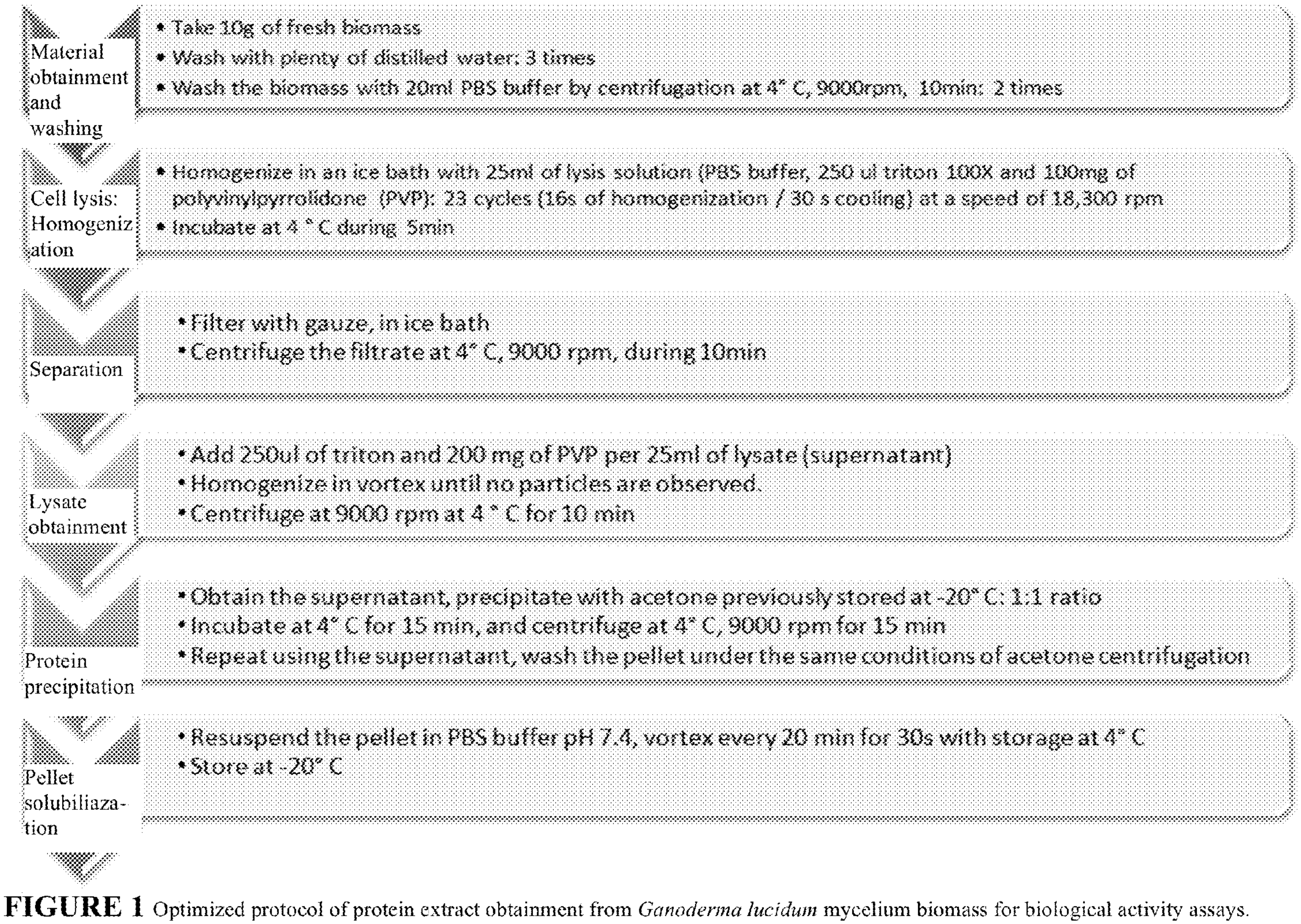
FIGURE 1 Optimized protocol of protein extract obtainment from *Ganoderma lucidum* mycelium biomass for biological activity assays.

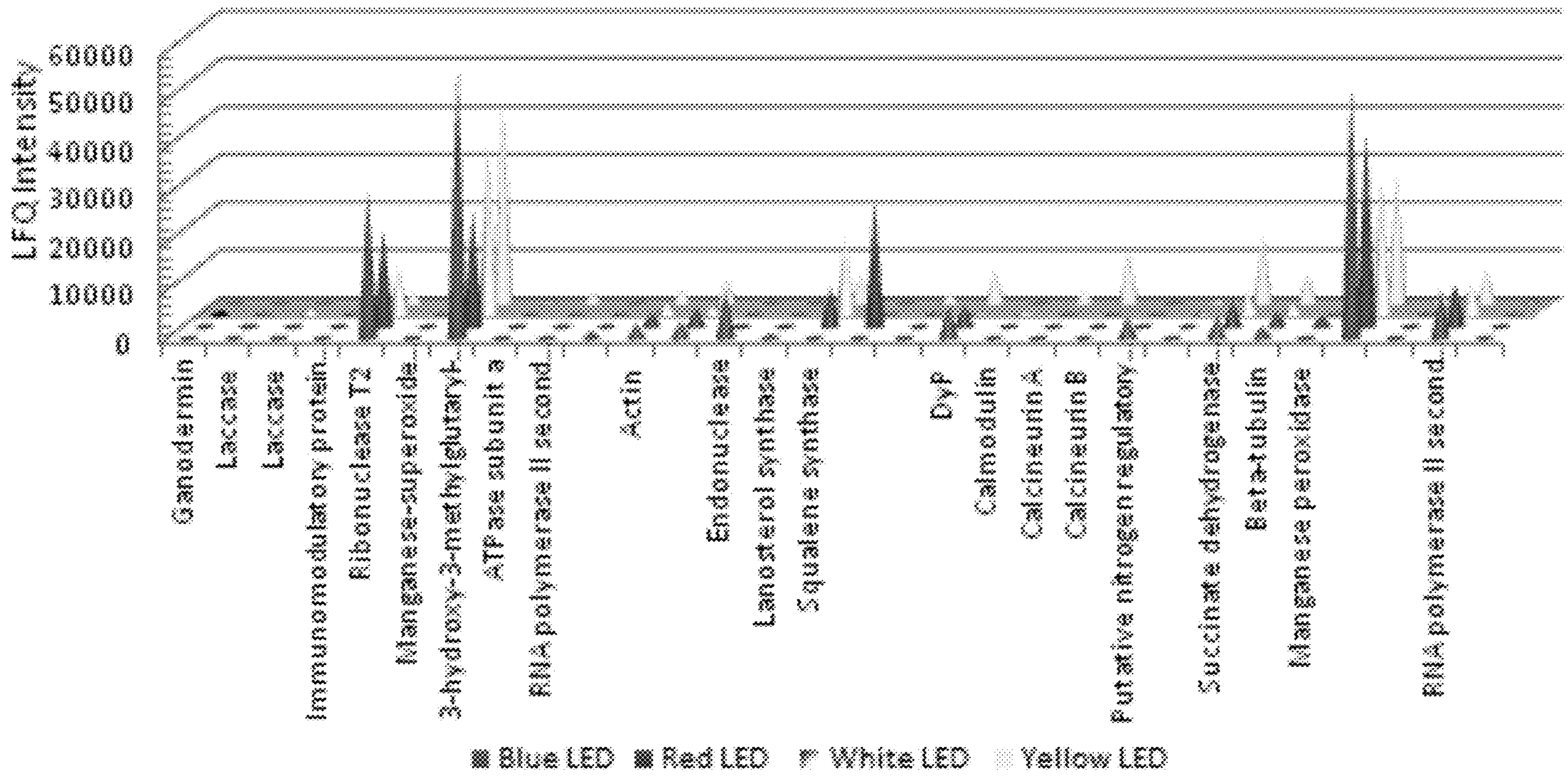
FIGURE 2 *Ganoderma lucidum* proteins identified in the different extracts when seeded under several LED light conditions, where their differential expression may be observed.

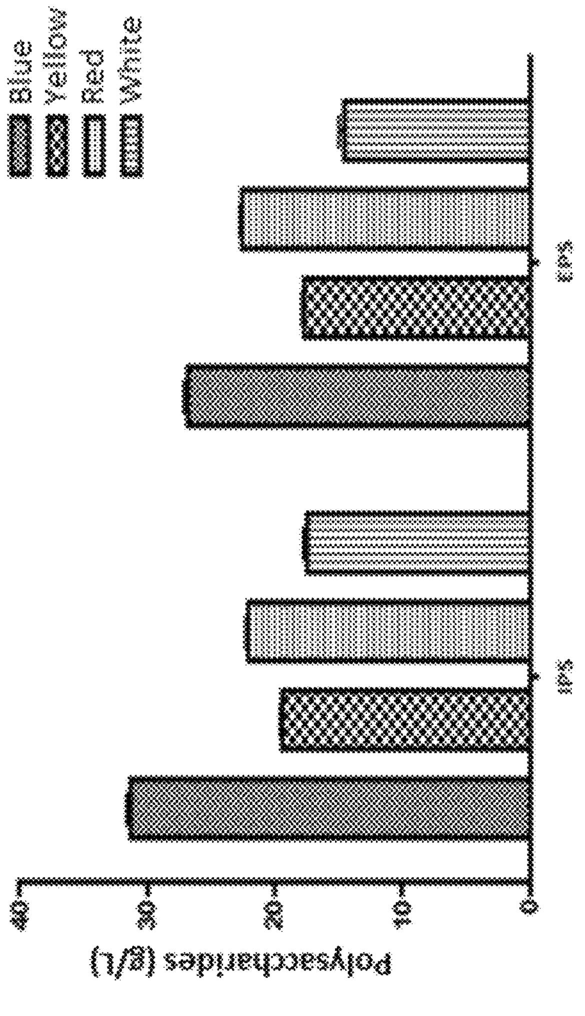
FIGURE 3 Obtainment of *Ganoderma lucidum* polysaccharides (IPS and EPS) when plated under different LED light conditions.

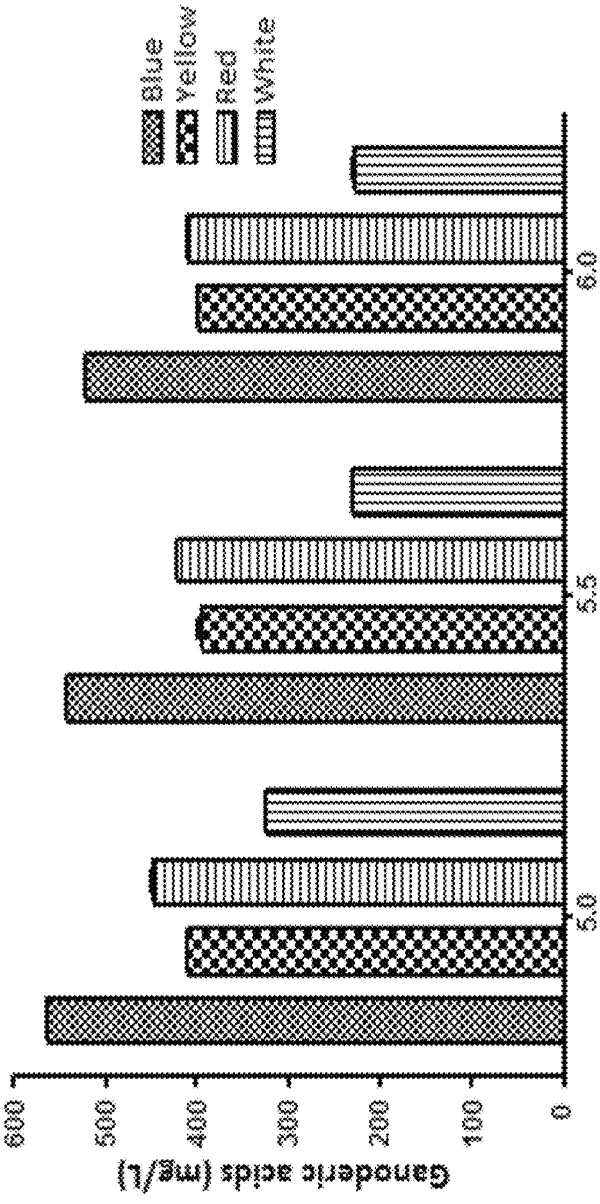
FIGURE 4 GA obtainment from *Ganoderma lucidum* when plated under different LED light conditions.

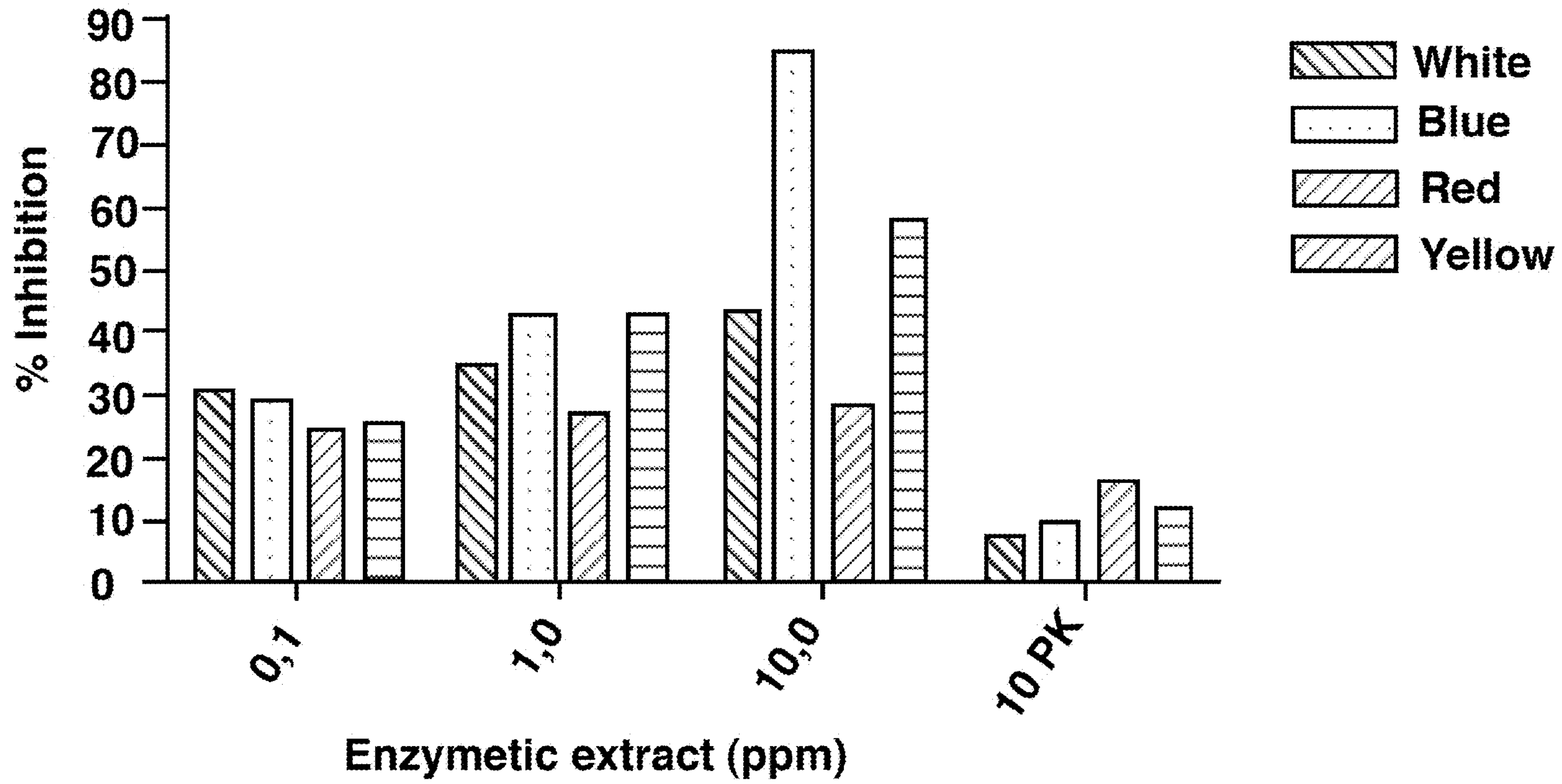
FIGURE 5: Figure illustrating results obtained for the *Mycosphaerella fijiensis* ascospore germination inhibition percentage for each extract and concentration thereof.

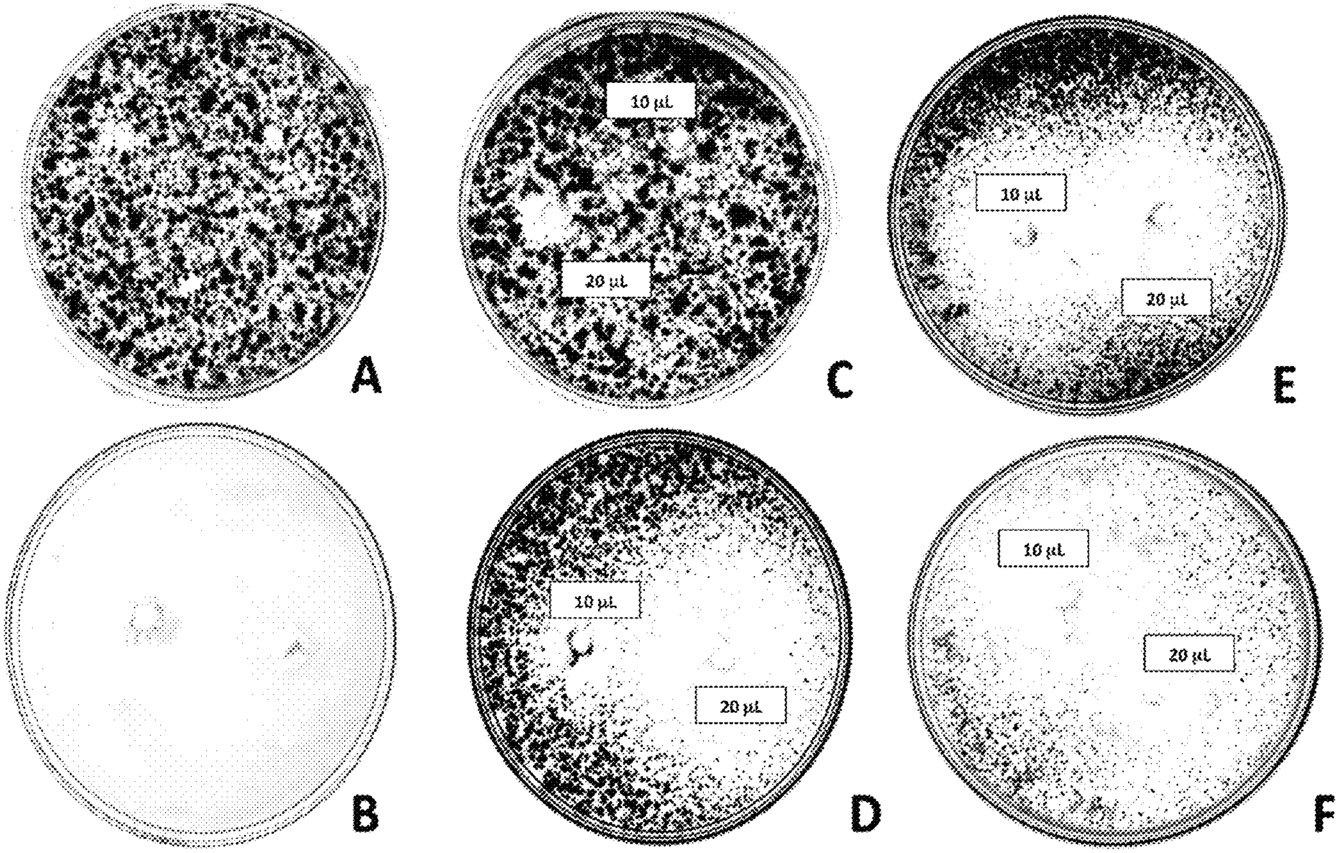

FIGURE 6. Evaluation of the different extracts using the agar diffusion test, wherein each plate was inoculated with *Mycosphaerella fijiensis* at a concentration of 2 x 104 mycelium fragments/ml (A) growth control (B) Mancozeb control (C) plate treated with white extract, having a small inhibition halo in the 10 µL well (D) plate treated with yellow extract, having an inhibition halo in the 10 µL and 20 µL well (E) plate treated with red extract, having an inhibition halo in the 10 µL and 20 µL well (F) plate treated with blue extract, having an inhibition halo in the 10 µL and 20 µL well

PROCESS FOR POTENTIATING THE PRODUCTION OF LINGZHI MUSHROOM (*GANODERMA LUCIDUM*) SUBSTANCES AND ANTIFUNGAL ACTIVITY THEREOF

PRIOR RELATED APPLICATIONS

This invention claims priority to CO 13-036699, filed on Feb. 22, 2013 and incorporated by reference in its entirety herein.

FIELD OF THE INVENTION

The present invention refers to a new process for potentiating the production of substances having antifungal activity obtained from *Ganoderma lucidum*, compositions containing said antifungal substances and their use as inhibitors of mycelium growth and fungi ascospore germination, amongst them those of *Mycosphaerella fijiensis*.

BACKGROUND ART

US2008/138875 describes a method for increasing the production of microorganism biomass, particularly *Ganoderma lucidum* from mycelium at a very low cost. The process is carried out within a closed system comprising a light source producing different wavelengths in order to obtain an increase in biomass; however, no mention of an increase in primary and/or secondary metabolites is given or any antifungal activity.

The publication "Electrical field effect on mycelium biomass production of the medicinal fungus *Ganoderma lucidum*" (*Actual Biol* 2010, 32 (92): p. 5-17) evaluates the effect of electrical fields, such as alternate current, continuous current, pulsated current and field intensity, on the growth of the fungus *Ganoderma lucidum* under submerged growth culture conditions, with the purpose of optimizing its biomass production.

The publication "Production of Biomass, Polysaccharides, and Ganoderic Acid using Non-conventional Carbon Sources under Submerged Culture of the Lingzhi or Reishi Medicinal Mushroom, *Ganoderma lucidum*" (International Journal of Medicinal Mushrooms 2012. Vol. 14. I. 2 p. 197-203), mentions the effect of the different non-conventional carbon sources in the *Ganoderma lucidum* growth, for the simultaneous production of mycelium biomass, ganoderic acids and polysaccharides, using non-conventional carbon sources in order to minimize the high costs of the current growth culture media. The publication does not disclose a process for increasing the obtainment of *Ganoderma lucidum* extracts or metabolites nor its antifungal activity.

DESCRIPTION

Strict biological control is defined as the use of live organisms as agents for plague and disease control and it is one of the most used methods for counteracting the use of agrochemicals. In the past few years, they have been used as an efficient alternative, those natural compounds obtained from microorganisms and plants, which have advantages over commercial chemical products, for being less toxic, both on the ecosystem as well as on the global population and because the same microflora in situ biodegrades them.

The well known medicinal properties of *Ganoderma lucidum* have lately driven a growing interest in all areas to study its metabolites and biological activities. Amongst the active compounds reported for this fungus are found β-D-glucane type polysaccharides, lanostane type triterpenoids known as ganoderic acids, proteins and peptides (1-4).

The *Ganoderma lucidum* fungus is widely known for its beneficial effects in humans; however, it has other properties such as its capacity to inhibit growth of phytopathogenic agents, such as *Botrytis cinerea, Fusarium oxysporum* and *Physalospora piricola*, which represents an interesting alternative in developing biocontrol products (5,6).

Black Sigatoka or the black stripe of bananas, is a disease caused by the Ascomycete fungus *Mycosphaerella fijiensis* (M. Morelet) (sexual form, heterothalic), which in its anamorphous stage is *Pseudocercospora fijiensis* (M. Morelet) Deighton (7). This fungus is a hemibiotrophic haploid found classified in class Dothideomycetes, order Capnodiales and family Mycosphaerellaceae. *Mycosphaerella fijiensis* (and its anamorphous *Pseudocercospora fijiensis*), is considered the most devastating species of the complex termed 'Sigatoka disease complex' (8-9).

The first symptoms of the disease are numerous and upon examination of the leaves throughout the different stages and comparing them to a healthy leaf it is possible to observe the accumulated deterioration of the tissues, observing that the initial change is carried out around the aereous space and continues to spread towards the parenchyme cells and vascular bundles, finally the mesophyll tissue degrades and the entire structural conformation of the leaf is lost (9).

The fungus *Mycosphaerella fijiensis*, arrives at the leaf in ascospores and conidiums and then continues to germinate towards the stomas, which are invaded by the mycelium until they are entirely covered with the different fungus structures (9). 1 mm diameter greenish dots appear in the plant's leaf which continues to develop into 2 to 3 cm long thin greenish reddish stripes, visible in the leaf's haz; then the spots join and darken until reaching a black color. Finally, the dead and black zones dry up and acquire a more pale color. Affected leaves may die in three to four weeks and the result is a rapid and severe weeding (9).

Disease control and management is basically found in cultural practices using weeding, thinning, trimming and intensive application of chemical fungicides, among them, demethylation inhibitors (DMIs), amines, Qo inhibitors (QoIs), anilinopyrimidines (APs), benzimidazoles (BCMs), SDHI fungicides and guanidines, especially in technified crop fields. Despite the efforts, disease control is ever so difficult given the fungus' capacity to grow and successfully adapt to the ecosystem conditions of the banana crop field sites, making ridding of the disease ever more so difficult.

There is therefore a need to find agents and active ingredients for the biological control using a plethora of antagonistic mechanisms against the pathogen, with which making disease control commercial formulation would result feasible and thus being able to attack the pathogenic agent from different fronts.

It is well known that a large part of substances or metabolites obtained currently for biological control processes are obtained from traditional culture crops, and on a laboratory scale, wherein occasionally, optimized culture media do not exist for the production of biomass and bioactive ingredients.

In order to find a new alternative for the management of black sigatoka, through the use of biological control techniques and the obtainment of active extracts, the inventors developed an optimized process for increasing the production of *Ganoderma lucidum* biomass and antifungal active ingredients thereof as inhibitors of mycelium growth and fungi ascospore germination, particularly *Mycosphaerella fijiensis*.

Therefore, in a first aspect, the instant invention provides a process, which initially comprises a *Ganoderma lucidum* obtainment stage in an adequate culture medium and specific environmental conditions which generate an unforeseen increase in biomass production in a reduced time.

After the obtainment process, a cell lysis stage is carried out in order to extract active compounds with which the final concentration of total active substances is increased. The protein extracts obtained during the process, were evaluated on ascospore germination and *Mycosphaerella fijiensis* mycelium growth, unforeseeably finding a detrimental effect of the phytopathogen when being potentiated through the process of the invention.

In another aspect, the instant invention implements the use of a technological device for the differential, qualitative and quantitative expression of proteins and other bioactive molecules of *Ganoderma lucidum*, selected from the group consisting of polysaccharides, triterpenoids, fatty acids and ganoderic acids. The invention provides for an unforeseen increase in the production of polysaccharides (intra and ex polysaccharides), triterpenoids, fatty acids and ganoderic acids.

In an additional aspect, the instant invention provides a protein extract, an ethanol extract and a triterpenoid-rich and fatty acid-rich *Ganoderma lucidum* extract exhibiting antifungal activity, particularly against *Mycosphaerella fijiensis*. The protein extract comprises at least one protein family from the protease, peroxidase, nuclease, lacase, immunomonuclease, phosphatase, dehydrogenase, synthase, oxidase, polymerase, and demthylase groups exhibiting substantial inhibition against *Mycosphaerella fijiensis*.

In another aspect, the current invention provides a formulation comprising the ethanol extract, the triterpenoid-rich and fatty acid-rich extract and the protein extract, or one or more proteins from the *Ganoderma lucidum* protein extract, together with an agrochemically acceptable carrier.

In another aspect, the present invention provides the use of *Ganoderma lucidum* as a *Mycosphaerella fijiensis* mycelium growth antagonist fungus.

In an additional aspect, the instant invention provides for the use of the protein extract and/or the ethanol extract and/or the triterpenoid-rich and fatty acid-rich *Ganoderma lucidum* extract for the inhibition of mycelium growth and pathogen ascospore germination, particularly *Mycosphaerella fijiensis*, in conventional and non-conventional crop fields.

DETAILED DESCRIPTION

Maintenance of the *Ganoderma lucidum* Strain and Conservation Thereof in a Petri Dish The *Ganoderma lucidum* strain (donated by Dr. ST. Chang from the Plant Biotechnology Laboratory from the Universidad de Antioquia) was maintained in a potato dextrose agar (PDA) at 4° C. (working strains, first subculture from a laboratory mother strain) (10-12).

The process followed consisted in taken 1 cm culture media and mycelium squares were transferred to petri dishes having solid MGL1 medium, comprising (g/L): barley flour 30.0 g; yeast extract 3.0 g; sucrose 5.3 g and agar-agar 8.0 pH-adjusted to 5.5±0.1 (11,12).

*Ganoderma lucidum* Mycelium Biomass Obtainment Under Submerged Culture Conditions Using Different LED-Based Lighting Systems.

1 cm diameter mycelium and agar discs were inoculated in 250 ml flasks having 50 ml culture medium, comprised of liquid MGL1: $NaNO_3$ 80 mg/L; $KH_2PO_4$ 30 mg/L; $MgSO_4.7H_2O$ 20 mg/L; KCl 10 mg/L supplemented with 50 g/L barley flour at a pH 5.5±0.1 (11, 12). The inoculated media were incubated at 100 rpm, 25±1° C., during 5 days of culture. From this pre-inoculum, 1 gram of biomass was transferred and inoculated in 250 ml Erlenmeyers having 60 ml of the same medium. This media was incubated with continuous stirring at 100 rpm, 25±1° C., and treated under different LED light conditions (white, blue, red, yellow) for each one of the assays, during 9 days of culture (11,12).

Extract from Mycelial Biomass of *Ganoderma lucidum* Extract from Cultivated Under Different LED-Based Wavelengths: Proteins, Polysaccharides, Ganoderic Acids, Triterpenoids and Fatty Acids.

Protein Extracts

Protein Extract without the Optimization Process 10 grams of fresh biomass from each of the culture media grown under different LED light conditions, was washed 3 times using abundant distilled water, later was washed twice using 20 mL PBS phosphate buffer pH 7.4 by centrifugation at 4° C., 9000 rpm during 10 minutes (Boeco® U320R) (12). Furthermore, the biomass was sonicated in an ice bath and later the filtrate was centrifuged at 4° C., 9000 rpm, during 10 minutes. The recovered supernatant was treated with 250 μL triton and 200 mg PVP for each 25 ml of lysate, everything was homogenized in a vortex until no particles could be observed in the solution and was again centrifuged at 4° C., 9000 rpm, during 10 minutes.

Finally, acetone was added to the recovered supernatant, previously stored at −20° C., in a 1:1 ratio incubated during 1 hour at 4° C. Later, centrifugation was carried out at 4° C., 9000 rpm during 15 minutes; this last precipitation step was repeated once again with the supernatant. The pellet obtained was again washed using previously chilled acetone at −20° C. and strong vortex was carried out for the dispersion of the pellet. Centrifugation at 4° C., 9000 rpm during 30 minutes was carried out. The supernatant was discarded and the pellet re-suspended in 3 ml PBS buffer pH 7.4. Further, the protein extracts stemming from each light condition were quantified by the Bradford method, aliquoted and stored at −20° C. (53-55).

Optimization of the Protein Extraction Conditions of the *Ganoderma lucidum* Mycelium Biomass The methodology used for obtaining protein extracts from *Ganoderma lucidum* mycelium biomass is described below. As may be noted, the methodology implemented makes use of sonication as a method of cellular lysis, primarily for cell wall rupture. In order to optimize the extraction of mycelium proteins, the effect of two cell lysis processes and the combination thereof were first evaluated (sonication, homogenization, and both), and later, optimization of rupture conditions with the selected process was carried out. FIG. 1 describes the optimized obtainment process of the *Ganoderma lucidum* protein extracts.

Qualitative and Quantitative Protein Expression

For this assay in particular, 10 μg of each of the *Ganoderma lucidum* protein extracts were taken, coming from different culture conditions, White LED, Blue LED, Yellow LED, and Red LED, in triplicate and a one-dimension electrophoresis was run. Later, all present proteins were excised en each 1D electrophoresis column in order to assay them using mass spectrometry and further analysis and identification by sequence comparison in the several different databases using MASCOT.

The methodology used in this study can be summarized in 5 steps after running the proteins on the gel: (i) unstain the gel, (ii) reduce disulfide bridges and alkylate resulting sulphidryl groups, (iii) enzymatically direct proteins using trypsin, (iv) extract resulting peptides and (v) assay using mass spectrometry (13-15). The technique used allowed for relative quantification of the proteins found, carrying out comparisons of proteins profiles according to relative intensities of the chromatograms of extracted ions during the enzymatic digest (16-19).

Crude Ethanol Extract 50 grams of dry and pulverized biomass was ground in 96% alcohol for two hours in ultrasound (Misonix®). Later the material was filtered and dried in a rotoevaporator, weighed and stored at 4° C. for later use.

Polysaccharide Extraction and Quantification: IPS (Intapolysaccharides) and EPS (Exopolysaccharides)

For IPS quantification, 1 g of dry *Ganoderma lucidum* mycelium biomass was taken and was re-suspended in 10 mL of water. This blend was taken to the autoclave for high-temperature extraction; the hot solution was filtered. Further, IPS precipitation was carried out by diluting the filtrate in four 96% ethanol volumes at 4° C. during 1 hour, followed by 4000 rpm centrifugation. The pellet obtained was diluted in 5 mL of water and used for centrifugation using the validated Phenol-Sulfuric Acid method (20). For EPS extraction, the filtered medium was centrifuged at 2500 rpm at 25° C. in order to eliminate suspended solids; 10 mL of the supernatant was taken and four 96% ethanol volumes were added. The same protocol was carried out for IPS extraction in order to obtain the polysaccharide extract.

Ganoderic Acid (GA) Extraction and Quantification

For GA quantification, the basic process followed was taking a dry mycelium biomass sample (500 mg), to which 50% (v/v) ethanol was added. Later, centrifugation at 2500 rpm for 15 minutes was carried out; the supernatant was dried by vacuum evaporation at 40° C., the residue re-suspended in water and extracted using chloroform. The GA in chloroform were extracted with 5% bicarbonate, 2M HCl was added to the basic aqueous phase until the pH was adjusted to values less than 3 and ultimately, it was extracted using chloroform, which was dried by vacuum evaporation at 40° C. The residue was again dissolved in absolute ethanol and was read at a 245 nm absorbance.

Triterpenoid and Fatty Acid Extraction, Characterization and Relative Quantification 100 g of freeze-dried biomass and 100 g of freeze-dried wasted extracellular medium from each of the LED-light treatments were taken and subject to maceration using 200 ml of $CH_2Cl_2$ during 5 days. Later, solvent removal was carried out every two days, until the Liebermann Burchard qualitative test, which is Δ5-sterol-specific or specific for sterols containing real or potentially conjugated dienes, turned out negative. The crude extracts were concentrated until dry in a rotoevaporator.

Thereafter, 1 g of each of the extracts was saponified in order to eliminate free fatty acids, as such: 20 ml of a 1M KOH in MeOH solution was added to the extract at 80° C. during 180 minutes, under reflux conditions. To the saponification product 10 ml of $H_2O$ was added and it was extracted using ethyl ether. The organic phase was washed with water until reaching a neutral pH, in order to then be collected on anhydrous sodium sulfate and concentrated until dry in a rotavapor.

The chemical characterization of the extracts was carried out using gas chromatography coupled to mass spectrometry (GC-MS). The equipment specs are as follows: HP6890, internal ZB-5HT capillary column (30 m, 0.25 mm ID and 25 μm thickness), carrier gas He 4.5 to 1.1 mL/min, Splitless injection mode and injector temperature 300° C. Said chromatograph unit was coupled to a 5973 mass detector, with a 70 eV ionization source.

The program used consisted of a heating ramp of 60° C. during one minute and later 7.4° C./min until reaching 310° C. 1 μL of each extract was injected into 3 mg/mL of $CH_2Cl_2$. The components were identified by comparison with the equipment log and as for the triterpenoid components, by analysis and comparison with databases of the Macromycete Fungus Chemical Research Group of the Universidad Nacional de Colombia.

*Mycosphaerella fijiensis* Isolations and Monospore Cultures Obtention for Assays

*Mycosphaerella fijiensis* isolations were performed by colleting ascospores from infected plant material (previously diagnosed at Cenibanano-AUGURA and submitted by Cenibanano to the Biotechnology Laboratory at Universidad de Antioquia (21-23). Lesions found on leaves classified for a stage 6 of the disease according to the Fourèscale (1985) characterized by foliar grayish white spots with black dots, which under an electronic microscope evidenced the presence of pseudothecia for ascospore dispersion and conidiophores for the release of conidia (23).

Ascospores were identified under a binocular compound microscope with a number 20 objective; they were selected one by one in order to be transferred to a PDA medium and then incubated at 25±1° C. until obtaining the colony named R1. A subculture was finally performed, the colonies obtained were divided and sub-cultured in PDA medium as work isolations R2 (24).

Antagonism Assay Using Deep Planting of *Mycosphaerella fijiensis*

A 1 cm diameter disc of a *Mycosphaerella fijiensis* R2 culture was inoculated, previously macerated in a 0.9% NaCl solution, in Petri dishes with the MGL1 culture medium melted at a temperature of 37° C. This culture was incubated for a lapse of 15 days in the dark at room temperature. Later, a 1 cm diameter disc of *Ganoderma lucidum* was inoculated on *Mycosphaerella fijiensis* grown mycelium; said dual culture was incubated for a lapse of 15 days in the dark at room temperature. The assays were performed in triplicate using a *Mycosphaerella fijiensis* growth control and a *Ganoderma lucidum* growth control. The cultures were microscopically assayed during the course of the experiment, observing and comparing the hyphae of each one of the fungi.

Antagonism Assay in Dual Plates: Antagonism Assay by Facing *Ganoderma lucidum* vs. *Mycosphaerella fijiensis*

A 1.3 cm diameter disc of a *Mycosphaerella fijiensis* R2 culture was inoculated, in Petri dishes with PDAL culture medium, at a distance of 2 cm from the dish edge and incubated at room temperature for 20 days, in order to provide the phytopathogen all optimal growth conditions for its establishment and substrate colonization.

After this time lapsed, a *Ganoderma lucidum* 1.3 cm diameter mycelium disc was inoculated in each culture medium, at a 4.5 cm distance from the *Mycosphaerella fijiensis* colony (26, 27, 33-36). Finally, this dual culture was incubated for 26 days in darkness at room temperature. The assays were performed in triplicate using a *Mycosphaerella fijiensis* growth control and a *Ganoderma lucidum* growth control. Cultures were macroscopically assayed during the course of the experiment, using a millimetric ruler for measuring the radius of the *Mycosphaerella fijiensis* colony (26,32). Inhibition percentage was assayed at 15 days of the antagonism, according to the mathematical model described for this type of analysis defined as RG=(G/G1)×100, wherein G is the treatment's growth efficiency and G1 the control, obtained from the following ratio:

G1=(FD/ID)

Wherein,

FD=final diameter of the colony, ID=initial diameter of the colony (37).

Additionally, samples from each treatment were taken, both observed by light microscope as well as electronic microscope, in order to compare morphological variations of the phytopathogenic fungus upon exposure to the controlling fungus (26, 27, 33-36). The samples were initially observed on a light microscope using 40× and 100× objectives (Nikon, Microscope eclipse 80i) and images were taken using a Nikon N is Elements BR 3.2. imager. Samples of the control *Mycosphaerella fijiensis* mycelium and antagonized *Mycosphaerella fijiensis* were taken, deposited on a cover slip and staining a 5% red congo dye (39).

For the observation using a scanning electron microscope SEM (Jeol, JSM 6490LV Model), control and antagonized *Mycosphaerella fijiensis* mycelium samples were taken. Samples were fixed using the FAA protocol (45% of 95% ethanol, 45% glacial acetic acid, 10% formaldehyde (44-48)). The samples were freeze-dried and adhered to the sample holder using electric tape and coated using a vacuum gold film by sputtering for two minutes (Denton Vacuum, Desl IV model) (49-51).

Finally, control and antagonized *Mycosphaerella fijiensis* mycelium samples were taken when under the effect of *Ganoderma lucidum*, in order to determine the feasibility of the *Mycosphaerella fijiensis* mycelium. Part of the antagonized *Mycosphaerella fijiensis* mycelium was replicated in new Petri dishes with PDAL medium, in order to observe the development of the mycelium and new *Mycosphaerella fijiensis* hyphae. Furthermore, a 0.8 mM in PBS trypan blue exclusion test was carried out, a widely used method to differentiate between live cells and dead cells, since trypan blue is a supravital stain that colors dead cells. The mycelium was macerated in the presence of the stain and the samples were observed under 40× and 100× objectives (Nikon, Microscope eclipse 80i) and the images taken using a Nikon N is Elementes BR 3.2 imager.

Antifungal Activity Assays on Ascospore Germ Tube Elongation

In order to carry out this assay, ascospores were collected where in each Petri dish, containing water agar (2%), the extract to be studied in each of the different concentrations was added (ethanol extracts; 0, 100 ppm, 1000 ppm, 10000 ppm and protein extracts: 0, 0.1 ppm, 1.0 ppm, 10 ppm). Furthermore, a 10 ppm protein extract+K proteinase (E.C. 3.4.21.64) was assayed (56, 57).

This is primarily used in this type of assays as a means of controlling that the activity found in fact corresponds to the activity of one or various extract proteins and not other substances that may be extracted during the process. For this purpose, the enzyme was added to the raw protein extract at a final concentration of 20 mg/ml. The extracts were incubated at 37° C. for an hour using a vortex every 10 minutes, then the extracts were centrifuged at 9000 rpm, 4° C. during 15 minutes; the freeze-dried supernatant of each extract was used to carry out the activity assays (59, 60).

Finally, after carrying out the ascospore discharge during 45 minutes in each of the extract-supplemented media, leaves were removed and media was incubated for 48 hours at 25±1° C. The ascospores were measured using a micrometer and germ tube lengths were recorded (Nikon Stage Micrometer), under a binocular compound microscope using a 20× objective (Nikon, Microscope eclipse 80i). All assays were carried out in triplicate, measuring 60 ascospores per treatment, in at least five discharge fields (59, 60). Inhibition percentage of the extracts was calculated taking the ascospores developed in water agar as control.

All results were analyzed using Statgraphics XV.I. For the ethanol extract assay, a one way ANOVA was carried out, wherein the factor assayed was the extract concentration. For the protein extracts, a one way block design was performed wherein the effect of different protein extracts was assayed at different concentrations. For each model, ANOVA and post-ANOVA tests were performed, in order to assay the givens.

Fungicide Activity Evaluation of *Ganoderma lucidum* Extracts: Mycelium Growth Inhibition in Microplate Format Fungicide Activity Evaluation of *Ganoderma lucidum* Protein Extracts In order to obtain protein extracts, the optimized protein extraction protocol was followed (Item 4.1.2). Later, the protein pellet was re-suspended in 1 ml PBS pH 7.4 buffer, 200 μL DMSO and 200 μL glycerol. The protein extracts of each LED were quantified by the Bradford method (Bio-Rad Protein Assay®) (61). Starting from stock solutions, 100 μL of each one of the *Ganoderma lucidum* protein extracts were added for a final concentration in the 500, 250, 125 and 100 ppm plates. The extracts were diluted in pH 7.4 PBS phosphate buffer.

The *Mycosphaerella fijiensis-inoculated* microplates and also treated with the different extracts were incubated. Readings were performed according to the Standard Norm. Each concentration was assayed in three repetitions, including three experiment replicas (63, 64). Thereafter, the determination of the growth inhibition percentage for each concentration of each protein extract used was performed (65-67).

Fungicide Activity Evaluation of Triterpenoid and Fatty Acid-Rich *Ganoderma lucidum* Extracts In order to obtain the triterpenic extracts, the protocol described in section 4.3 was followed. Later, the extracts were prepared at a 100,000 ppm concentration and dissolved in a 1:1 Ethanol:DMSO mix. The microplates were inoculated with *Mycosphaerella fijiensis* according to the conditions previously established. Thereafter, several dilutions from the stock solutions were performed in the microplate, in order to assay the antifungal activity of the extracts at final concentrations of 5000, 4000, 3000, 2000, and 1000 ppm, pursuant to the Standard Norm. Each concentration was assayed in 3 repetitions, including three experiment replicas (63, 64). Thereafter, the determination of the growth inhibition percentage for each concentration of each extract concentration used was performed (65-67).

Antifungal Activity Assay of Extracts Using the Agar Diffusion Technique: Protein Extracts and Triterpenoid and Fatty Acid-Rich Extracts.

In order to corroborate antifungal activity of each extract, said activity was assayed in Petri dishes using the plate diffusion method; for said purpose, 20 ml of PDA medium were dispensed for a final thickness of 4 mm. After homogenizing inocula, deep plating was performed wherein each plate was inoculated using $2\times10^4$ *Mycosphaerella fijiensis* mycelium fragments. Afterwards, using a 0.5 mm internal diameter punch, wells were made wherein 10 or 20 μL of each extract were deposited, in addition to the inhibition positive control using Mancozeb and a negative control using a 1:1 ethanol: DMSO mix. The plates were incubated in darkness conditions, 25±1° C. for seven days.

EXAMPLES

Protein and Other Bioactive Ingredient (Polysaccharides, Triterpenoids, Ganoderic Acids and Fatty Acids) Qualitative and Quantitative Expression Using a Technological Device Based on Different Electromagnetic Radiation Wavelengths Proteins A list of molecular masses was obtained herein measured using mass spectrometry, that were subject to MASCOT proteomic analysis program for comparison with the different proteins found in databases, and where a 34 protein list was able to be obtained, all of which have several expression degrees under the different light conditions, in the different extracts assayed. This allowed for a series of comparisons and to demonstrate that the light conditions under which the fungus is subject to for its growth indeed influences it in its production and protein expression at some point. Table 1 shows the list of identified proteins, initially indicating their physicochemical characteristics.

TABLE 1

Proteins identified in the *Ganoderma lucidum* extracts and some important characteristics.

| N° | Entry Name | Protein Name | Length (aa) | Weight (kDa) | Isoelectric Point (pI) |
|---|---|---|---|---|---|
| 1 | GANOD_GANLU | Ganodermin* | 27.0 | 2.72 | 10.28 |
| 2 | Q710F5_GANLU | Laccase | 299 | 32.03 | 5.03 |
| 3 | B5G553_GANTS | Laccase | 521 | 56.42 | 5.46 |
| 4 | LZ8_GANLU | Immunomodulatory protein Ling Zhi-8 | 111 | 12.51 | 5.09 |
| 5 | A6P7J5_GANLU | Ribonuclease T2 | 304 | 33.49 | 4.89 |
| 6 | D7F2S3_GANLU | Manganese superoxide dismutase | 142 | 15.45 | 8.76 |
| 7 | B2KX91_GANLU | 3-hydroxy-3-methylglutaryl-coenzyme A reductase | 1226 | 13.11 | 8.23 |
| 8 | B3XZ37_GANLU | ATPase subunit a | 175 | 19.31 | 8.94 |
| 9 | B3XZA5_GANLU | RNA polymerase II second largest subunit | 287 | 32.76 | 8.20 |
| 10 | B6UPH5_GANLU | Cytochrome c oxidase subunit 2 | 72 | 7.78 | 4.79 |
| 11 | Q2HPQ0_TRIHA | Actin | 257 | 28.83 | 5.24 |
| 12 | C7EWL6_GANLU | G-protein complex beta subunit | 313 | 34.90 | 5.79 |
| 13 | Q8HE45_GANLU | Endonuclease | 264 | 31.03 | 8.54 |
| 14 | D7NJ68_GANLU | Lanosterol synthase | 726 | 82.87 | 6.33 |
| 15 | A0SJQ5_GANLU | Squalene synthase | 467 | 54.01 | 7.09 |
| 16 | D8UZT0_9PEZI | RNA polymerase II second largest subunit | 351 | 39.68 | 6.13 |
| 17 | D8Q297_SCHCM | Farnesyl-diphosphate synthase | 347 | 39.82 | 5.65 |
| 18 | GOX8C9_GANLU | DyP | 488 | 53.19 | 7.7 |
| 19 | E7E161_GANLU | Calmodulin | 149 | 16.88 | 4.20 |
| 20 | E7E162_GANLU | Calcineurin A | 339 | 37.02 | 5.34 |
| 21 | E7E163_GANLU | Calcineurin B | 161 | 18.19 | 4.67 |
| 22 | F6M3U4_GANLU | Putative nitrogen regulatory protein | 265 | 28.92 | 9.65 |
| 23 | G1ECM7_GANLU | Calcineurin responsive zinc-finger CRZ1 | 639 | 69.21 | 8.79 |
| 24 | G3LGR3_GANLU | Succinate dehydrogenase iron-sulfur protein | 245 | 28.00 | 8.9 |
| 25 | B8K207_GANLU | Beta-tubulin | 120 | 13.34 | 5.87 |
| 26 | C0IMT8_GANLU | Manganese peroxidase | 364 | 38.11 | 4.61 |
| 27 | Q4PS64_GANTS | Translation elongation factor 1-alpha Q4PS64 Elongation factor 1-alpha | 379 | 41.43 | 8.73 |
| 28 | Q0GZR4_GANLU | Glyceraldehyde-3-phosphate dehydrogenase | 337 | 36.06 | 6.45 |
| 29 | B3XZA5_GANLU | RNA polymerase II second largest subunit | 287 | 32.76 | 8.20 |
| 30 | B4YA15_GANLU | Farnesyl-diphosphate synthase | 360 | 41.01 | 5.34 |
| 31 | B5G551_GANLU | Laccase | 520 | 56.26 | 5.16 |
| 32 | B5G552_GANLU | Laccase | 520 | 56.295 | 5.09 |
| 33 | B6E1X1_GANLU | Lanosterol 14-alpha-demethylase | 180 | 21.026 | 6.8 |
| 34 | Q0GZR4_GANLU | Glyceraldehyde-3-phosphate dehydrogenase | 337 | 36.067 | 6.45 |

*Corresponds to a peptide

The influence of the wavelength based on LEDs could differentially be observed on the *Ganoderma lucidum* protein profile, according to its expression level, in terms of intensity, obtained through mass spectrometry. FIG. 2 comparatively illustrates these expression levels for each protein identified.

It can be observed that the greater intensity (LFQ intensity), which can be interpreted as the greater concentration of the different proteins identified, shows on the yellow LED, followed by the blue LED, then the red LED and finally the white LED condition. This demonstrates that a differential effect does indeed exist when the fungus is exposed to different wavelengths, which ultimately is expressed in greater or lesser production of biomass quantity and the obtainment of polysaccharide and ganoderic acid-type primary or secondary metabolites.

Polysaccharide Quantification (IPS and EPS)

After performing the different assays using several light conditions, it was determined that the best light conditions for IPS and EPS production was blue LED light, with significant differences over the other conditions, with $p<0.05$ (FIG. 3).

Values obtained for IPS were: for blue LED light 31.32±1.24 g/L, followed by red LED light with 22.34±1.24 g/L, yellow light 19.23±1.24 g/L and finally white LED light with 17.42±1.24 g/L. Values obtained for EPS were: for blue LED light 29±2.31 g/L, followed by red LED light 22.33±2.31 g/L, yellow light 18.54±2.31 g/L and finally white LED light with 16.03±2.31 g/L.

Ganoderic Acid (GA) Quantification

It was determined that the best wavelength for GA production was the wavelength corresponding to blue light with a pH of 5.0 and a p value >0.05, obtaining 563.9±11.63 mg/L for blue LED light, followed by 447.1±11.63 mg/L for red LED light, 411.0 mg/L±11.63 for yellow LED light and finally 228.8 mg/L±11.63 for white LED light (FIG. 4).

Chemical Characterization and Relative Quantification of Triterpenoid and Fatty Acid-rich Extracts

TABLE 2

Relative abundance percentage of each compound in the *Ganoderma lucidum* extracts, plated under different LED light conditions.

| Compound | Intracellular (Relative Abundance %) Yellow LED | Blue LED | White LED | Red LED | Extracellular Relative Abundance %) Yellow LED | Blue LED | White LED | Red LED |
|---|---|---|---|---|---|---|---|---|
| Palmitic acid | 7.60 | Tz | 31.20 | 16.40 | 14.36 | 9.94 | 2.92 | 5.72 |
| Ethyl palmitate | 1.70 | 27.70 | 7.90 | 7.80 | 5.88 | 9.75 | 13.85 | 3.31 |
| Ethyl linoleate | 12.20 | 39.50 | 11.70 | 23.50 | 32.43 | 29.19 | 33.97 | 10.94 |
| Ethyl oleate | 14.10 | 17.60 | 5.20 | 8.80 | 10.12 | 26.61 | 15.23 | 3.82 |
| 22E-ergosta 5,7,9 (22), tetraen 3β-ol | 1.30 | Tz | 0.35 | | | | | |
| Ergosta 5,7,22 trien 3β-ol | 2.20 | | 1.02 | | | | | |
| Ergosta-5-3β-ol | | Tz | | | | | | |
| Estigmast-5-3β-ol | 1.10 | 2.20 | 0.40 | 2.20 | | | tz | |
| 26,26-dimethyl 5, 23 ergostadien 3β-ol | | | Tz | | | | | |
| Estigmast-4 en-3-one | 2.30 | 4.30 | 0.70 | 2.80 | 2.51 | 1.42 | tz | 5.71 |
| Estigmast-5,24(28)-dien-3β-ol | 0.96 | | | | | | | |
| Estigmast-4,24(28)-dien-3-one | 0.78 | | | | 0.83 | | tz | 1.53 |
| 5α-Estigmast-3-one | | Tz | | | | | Tz | |
| (22R,24S)-22,24Dimethylcholesterol | | | | | | | | 2.52 |
| Fatty acid total | 7.6 | Tz | 31.20 | 16.4 | 14.3 | 9.0 | 2.9 | 5.7 |
| Total fatty acid esters | 28.0 | 84.8 | 24.8 | 40.1 | 48.4 | 65.5 | 62.8 | 18.9 |
| Total triterpenoids | 8.6 | 6.5 | 2.5 | 5.1 | 3.33 | 1.5 | 0 | 9.7 |

Antagonism Assay in Dual Plates

Table 3 illustrates the growth of each fungus when found seeded individually or control medium or when co-seeded. As for the *Ganoderma lucidum* control, a growth rate of 0.2983 cm/day was found, and the co-seed at 0.281 cm/day. For *Mycosphaerella fijiensis*, it was determined that the control growth rate was 0.1287 cm/day and the co-seed 0.059 cm/day. The above evidences that *Ganoderma lucidum* slightly reduces its growth rate in the co-seed, but nevertheless is capable of colonizing the entire substrate in the same time period, whereas for *Mycosphaerella fijiensis*, the impact is greater, demonstrating it is the antagonized organism during the process.

TABLE 3

Growth inhibition percentage of *Mycosphaerella fijiensis* comparing the growth of the antagonized isolation versus control.

| Assay | Colony diameter average (cm) Day 1 | 8 | 15 | Antagonism % |
|---|---|---|---|---|
| Antagonized *Mycosphaerella fijiensis* | 2.439 | 2.528 | 2.581 | 85.1 |
| *Mycosphaerella fijiensis* control | 2.411 | 2.686 | 2.997 | Control |

Ascospore Germination Inhibition Using Different Extracts Obtained from *Ganoderma lucidum* Mycelium Biomass Raw Protein Extract Evaluation of the effect of *Ganoderma lucidum* protein extracts was performed using one way ANOVA with blocking, wherein the factor assayed was the protein extract of the different LEDs and the block being the extract concentration. Having obtained the variance analysis results and adjustment tests (independence, normality and equal variance), an effect was noted over ascospore germination due to the type of extract and its concentration, with a p value <0.05.

The analysis indicates that the blue LED extract, at 10 ppm showed an inhibition percentage of 84.95±0.89%, followed by the inhibition percentage of the yellow LED extract at 10 ppm at of 58.52±0.89% (FIG. 5).

Furthermore, it could be noted that the treatment with 10 ppm of each extract digested with proteinase K (10 PK), significantly reduced the inhibition percentage to 7.6±0.89%. This suggests that the effect observed on *Mycosphaerella fijiensis* ascospores is due to a protein or protein complex that are digested with the enzyme and thus no activity is shown (59, 60).

Ethanol Extracts

The ethanol extract concentration effect over the *Mycosphaerella fijiensis* ascospore germination inhibition percentage was evaluated, wherein it was found that a significant inhibition effect indeed exists which is produced by the ethanol extract over *Mycosphaerella fijiensis* ascospore germination, which is dependent on concentration, with a p value <0.05. The formation of three significantly different homogeneous groups was observed, wherein the 10000 ppm concentration of the ethanol extract showed greater inhibition percentage at 98.4±0.51%.

Evaluation of Fungicide Activity of *Ganoderma lucidum* Extracts Over *M. Fijiensis* in Microplates Protein Extracts without the Optimized Extraction Process A multifactor ANOVA variance analysis was performed for inhibition percentage, where it was observed that the LED factor, extract concentration and interaction thereof have an effect over *Mycosphaerella fijiensis* growth with a p value <0.05, wherein it is observed that by having a control at 0% inhibition, Mancozeb at a 0.3 ppm concentration, it showed 72% inhibition, amount surpassed by the different extracts, except the white extract, at concentrations starting at 100 ppm. Likewise, it is corroborated that the activity observed is due to one or several extract proteins since when treated with proteinase K, no antifungal activity was shown, even at a 1000 ppm concentration.

Through the use of logic models (non linear regressions) the relationship between the concentration logarithm of each antifungal (x axis) versus inhibition percentage (y axis) was established thus obtaining the respective equations, for $EC_{50}$ analysis for each treatment at 5 concentrations, in order to determine the necessary concentration of each extract to reduce the population growth by 50% at an in vitro level. Table 4 shows $EC_{50}$ for all protein extracts obtained under different LED light conditions, obtained when plotting the concentration log versus inhibition percentage.

TABLE 4

$EC_{50}$ for each treatment, wherein data adjustment to the log (inhibitor) vs. response equation is shown.

| Data | Red | Yellow | White | Blue |
|---|---|---|---|---|
| | Log(Inhibitor) vs. Response | | | |
| $EC_{50}$ (ppm) | 114.28 ± 1.02 | 94.41 ± 1.07 | 295.80 ± 1.11 | 11.32 ± 1.07 |
| $R^2$ (equation adjust-ment) | 0.9993 | 0.9945 | 0.9924 | 0.9938 |

The above table shows that the phytopathogenic fungus response in treatments with extracts obtained under red LED and yellow LED are similar, having an $EC_{50}$ of 114.288±1.02 and 94.406±1.07 ppm, respectively. The white extract was the least effective with an $EC_{50}$ of 295.8±1.11 ppm, while the response obtained the extract under blue LED light was the most potent, with an $EC_{50}$ of 11.32±1.07 ppm, well below compared to the other treatments.

Fungicide Activity of *Ganoderma lucidum*-Optimized Protein Extracts

In order to determine which the best protein extract for *Mycosphaerella fijiensis* mycelium growth inhibition was, a statistical analysis using a category factorial design was performed. The multifactorial ANOVA variance analysis for inhibition percentage shows that the LED factor, extract concentration and the interaction thereof all have an effect over *Mycosphaerella fijiensis* growth with a p value <0.05. Further, $EC_{50}$ analysis was performed on each treatment on all four concentrations, in order to determine the necessary concentration of each extract in order to reduce the population growth by 50% at an in vitro level.

As may be noted on Table 5, $EC_{50}$ is found well below in comparison to the assayed dosages, and it is therefore concluded that these new protein extracts extracted under the optimized protocol, are more potent, allowing to claim this response in reference to being able to extract at greater concentration the active proteins. Table 5 shows the results obtained when plotting the concentration logarithm versus inhibition percentage and the model adjustment.

TABLE 5

$EC_{70}$ and $EC_{95}$ for each treatment, wherein data adjusted to the log(inhibitor) vs response equation is shown.

| Data | Yellow | Blue | White | Red |
|---|---|---|---|---|
| | Log (Inhibitor) vs. Response | | | |
| $EC_{70}$ (ppm) | 149.6 ± 0.08 | — | 421.7 ± 0.12 | 100.46 ± 1.12 |
| $EC_{95}$ (ppm) | — | 158.49 ± 1.85 | — | 251.18 ± 1.12 |
| $R^2$ (equation adjust-ment) | 0.9992 | 0.9964 | 0.9967 | 0.9921 |

Note:
the best treatment is highlighted.

As may be noted, the blue LED extract continues being the most active, where the minimum inhibition percentage generated by the extract is 73%, a response well above those found with the extracts before the extraction optimization. When performing an $IC_{95}$ analysis, it can be noted that only the blue LED and red LED extracts reach said potency of 158.49±1.85 ppm and 251.19±1.12 ppm, respectively.

As may be noted in previous treatments, there exists *Mycosphaerella fijiensis* mycelium growth inhibition when treated with the different protein extracts and it is noted that the red and blue extracts show greater inhibition in comparison to other treatments and growth control; likewise, Mancozeb's activity as control fungicide can be observed, where the fungus growth is entirely inhibited. These results are found to be in agreement with the microdilution assay and with the ascospore germination assays, where the blue extract always shows the greater activity.

Fungicide Activity of Triterpenoid and Fatty Acid-rich Extracts

Table 6 shows how the triterpenoid and fatty acid-rich extracts present *Mycosphaerella fijiensis* mycelium growth inhibition. The greater inhibition is shown with treatments stemming from blue LED extracts, followed by the treatments with yellow LED extracts. For white and red LED extracts, no significant growth inhibition was found in comparison to a growth control without extracts.

TABLE 6

| Intracellular extracts. $EC_{50}$ for each treatment, wherein data adjusted to the log(inhibitor) vs response equation is shown. | | | | |
|---|---|---|---|---|
| Data | Intra-cellular Red | Intra-cellular Yellow | Intra-cellular White | Intra-cellular Blue |
| Log(Inhibitor) vs. Response | | | | |
| $EC_{50}$ (ppm) | NA | 103250 ± 75.64 | NA | 4563 ± 35.78 |
| $R^2$(equation adjustment) | — | 0.9932 | — | 0.9932 |

NA. Does not apply since extracts were not active.

Agar Diffusion Assay

Finally, and seeking to corroborate what is observed in the microplates, the antifungal capacity was assayed using the dish diffusion technique. FIG. 6 shows the results obtained at this level, where different quantities of each one of the extracts were deposited at the greatest concentration, 500 ppm, using 10 μL or 20 μL per well.

As can be noted from previous treatments, *Mycosphaerella fijiensis* mycelium growth inhibition exists when treated with the different protein extracts or triterpenoid-rich extracts and it can be noted that the red and blue extracts show the greatest inhibition compared to the other treatments and the growth control; Mancozeb activity as control fungicide can also be observed, wherein fungus growth is entirely inhibited. These results are in agreement with the microdilution assay and with the ascospore germination assays, wherein the blue extract always shows the greatest activity.

Agrochemical Compositions

From biomass and *Ganoderma lucidum* extracts obtained according to the subject invention, compositions comprising *Ganoderma lucidum* and/or any of its extracts may be prepared, together with carriers, vehicles, and adjuvants acceptable for agrochemical applications, as well as the use of said compositions for controlling and/or fighting phytopathogens.

Compositions according to the subject invention can be provided in any appropriate form, for example, in powder, solution, suspension, granule form, amongst others.

DESCRIPTION OF DRAWINGS

FIG. 1 displays an optimized obtainment process of the *Ganoderma lucidum* protein extracts.

FIG. 2 compares *Ganoderma lucidum* proteins identified in the different extracts when seeded under several LED light conditions, wherein their differential expression may be observed.

FIG. 3 displays the IPS and EPS production from *Ganoderma lucidum* under different LED light conditions.

FIG. 4 displays the Ganoderic acids production from *Ganoderma lucidum* under different LED light conditions.

FIG. 5 illustrates the inhibition percentage for the *Mycosphaerella fijiensis* ascospore germination.

FIG. 6 is an evaluation of the different extracts using the agar diffusion test, wherein each plate was inoculated with *Mycosphaerella fijiensis* at a concentration of 2×10^4 mycelium fragments/ml and (A) growth control, (B) Mancozeb control, (C) a plate treated with a white extract, having a small inhibition halo in the 10 μL well, (D) plate treated with a yellow extract, having an inhibition halo in the 10 μL and 20 μL well, (E) plate treated with a red extract, having an inhibition halo in the 10 μL and 20 μL well, and (F) plate treated with a blue extract, having an inhibition halo in the 10 μL and 20 μL well.

BIBLIOGRAPHY

1. Wasser, S. P. (2002) Medicinal mushrooms as a source of antitumor and immunomodulating polysaccharides., *Applied microbiology and biotechnology* 60, 258-74.
2. Asatiani, M., Kachlishvili, E., Khardziani, T., Metreveli, E., Mikiashvili, N., Songulashvili, G., Tsiklauri, N., Wasser, S., and Elisashvili, V. (2008) Basidiomycetes as a source of antioxidants, lectins, polysaccharides, and enzymes, *Journal of Biotechnology* 136, 7-17.
3. Akavia, E., Beharav, a, Wasser, S. P., and Nevo, E. (2009) Disposal of agro-industrial by-products by organic cultivation of the culinary and medicinal mushroom *Hypsizygus marmoreus., Waste management* (New York, N.Y.), Elsevier Ltd 29, 1622-7.
4. Lewinsohn, D., Nevo, E., Hadar, Y., Wasser, S., and Beharav, A. (2000) Ecogeographical variation in the *Pleurotus eryngii* complex in Israel, *Mycological Research* 104, 1184-1190,
5. Wang, H., and Ng, T. B. (2006) Ganodermin, an antifungal protein from fruiting bodies of the medicinal mushroom *Ganoderma lucidum., Peptides* 27, 27-30,
6. Xu, X., Yan, H., Chen, J., and Zhang, X. (2011) Bioactive proteins from mushrooms., *Biotechnology advances*, Elsevier Inc. 29, 667-74.
7. Deighton, F. (1976) *Pseudocercospora Speg., Pantospora Cif.*, and *Cercoseptoria Petr., Mycological Papers* 140, 1-168.
8. Churchill, A. C. L. (2011) *Mycosphaerella fijiensis*, the black leaf streak pathogen of banana: progress towards understanding pathogen biology and detection, disease development, and the challenges of control., *Molecular Plant Pathology*, Wiley Online Library 12, 307-328.
9. Cenibanano. (2009) Proyecto especial Sigatoka (AUGURA, Ed.) lra edición, pp 6-25, AUGURA, Medellin-Colombia.

10, Leskosek-Cukalovic, I., Despotovic, S., Lakic, N., Niksic, M., Nedovic, V., and Tesevic, V. (2010) *Ganoderma lucidum*—Medical mushroom as a raw material for beer with enhanced functional properties, *Food Research International* 43, 2262-2269.

11. Zapata, P., Rojas, D., and Atehortua, L. (2012) Production of biomass, polysaccharides and ganoderic acid using non-conventional carbon sources under submerged culture of the *Ganoderma lucidum, International Journal of Medicinal Mushrooms In press*.
12. Zapata, P., Rojas, D., Ramirez, D., Fernandez, C., and Atehortua, L. (2009) Effect of Different Light-Emitting Diodes on Mycelial Biomass Production of Ling Zhi or Reishi Medicinal Mushroom *Ganoderma lucidum* (W. Curt.: Fr.) P. Karst. (Aphyllophoromycetideae), *International Journal of Medicinal Mushrooms* 11, 93-99.
13. Panchaud, A., Affolter, M., and Kussmann, M. (2012) Mass spectrometry for nutritional peptidomics: How to analyze food bioactives and their health effects., *Journal of proteomics*, Elsevier B.V. 75, 3546-3559.
14. Penque, D., Simoes, T., and Amado, F. (2011) Proteomics advances in the last decade: What is next?, *Journal of proteomics* 75, 1-3.
15. Jiang, L., He, L., and Fountoulakis, M. (2004) Comparison of protein precipitation methods for sample preparation prior to proteomic analysis, *Journal of Chromatography A* 1023, 317-320,
16. Harder, A. (2008) Sample preparation procedure for cellular fungi, *Methods in molecular biology* 425, 265-273.
17. Dong, H., Kemptner, J., Marchetti-Deschmann, M., Kubicek, C. P., and Allmaier, G. (2009) Development of a MALDI two-layer volume sample preparation technique for analysis of colored conidia spores of *Fusarium* by MALDI linear TOF mass spectrometry., *Analytical and bioanalytical chemistry* 395, 1373-83.

18. Yin, Q. Y., De Groot, P. W. J., De Koster, C. G., and Klis, F. M. (2008) Mass spectrometry-based proteomics of fungal wall glycoproteins., *Trends in microbiology* 16, 20-6.
19. Lau, B. F., Aminudin, N., and Abdullah, N. (2011) Comparative SELDI-TOF-MS profiling of low-molecular-mass proteins from Lignosus rhinocerus (Cooke) Ryvarden grown under stirred and static conditions of liquid fermentation., *Journal of microbiological methods*, Elsevier B.V. 87, 56-63.
20, DuBois, M., Gilles, K. a., Hamilton, J. K., Rebers, P. a., and Smith, F. (1956) Colorimetric Method for Determination of Sugars and Related Substances, *Analytical Chemistry* 28, 350-356.
21. Stover, R. H. (1983) The effect of temperature on ascospore germ tube growth of *Mycosphaerella musicola* and *Mycosphaerella fijiensis* var. *difformis, Fruits* 38, 625-628.
22. Fouré, E., Grisoni, M., and Zurfluh, R. (1984) Les cercosporiosis du bananier et leurs traitements. Comportemente des variétés. Etude de la sensibilité variétale des bananiers et plantains B *Mycosphaerella fijiensis* Morelet et de quelques caractéristiques biologiques de la maladie de rales noires au G, *Fruits* 39, 365-377.
23. Fourée, E. (1985) Les cercosporiosis du bananier et leurs traitements. Etude de la sensibilité variétale des bananiers et plantains à *Mycosphaerella fijiensis* Morelet au Gabon, *Fruits* 40, 393-399.
24. Madrigal, R., Arroyo, T., Astua, T., and Monreri, S. (2012) List of Monitoring Methods, *FRAC* (*Fungicide Resistance Action Committee*) 1, 1-3.
25. McDonald, J. H. (2009) Handbook of Biological Statistics Second edi., pp 127-202, Sparky House Publishing, Baltimore, Md., USA.
26. Ortiz, A., and Orduz, S. (2001) In vitro evaluation of *Trichoderma* and *Gliocladium* antagonism against the symbiotic fungus of the leaf-cutting ant Atta cephalotes, *Mycopathologia* 150, 53-60,
27. Viveros, J., and Castaño, J. (2006) Evaluación in vitro de extractos vegetales sobre *Mycosphaerella fijiensis* Morelet, *In Vitro* 14, 37-50,
28. Etebu, E., Pasberg-Gauhl, C., Gauhl, F., Ayibo, D., and Kalio, L. (2005) Efecto de la luz y aeracion sobre la esporulacion y crecimiento lineal de *Mycosphaerella fijiensis, Infomusa* 14, 24-25.
29. Jacome, L. H., and Schuh, W. (1993) Effect of Temperature on Growth and Conidial Production in-Vitro, and Comparison of Infection and Aggressiveness in-vivo among Isolates of *Mycosphaerella-Fijiensis* Var *Difformis, Tropical Agriculture* 70, 51-59.
30, Pineda, F., Uribe, S., Saldarriaga, Y., and Calle, J. (2003) Susceptibilidad de *Rhodnius pallescens* (Hemiptera: *Reduviidae*) de V estadío de desarrollo a la acción de *Beauveria* spp., *Entomotrópica* 18, 163-168.
31. Mira, J. J. (2004) Caracterización mediante métodos biológicos, de aislamientos de *Mycosphaerella fijiensis* Morelet, resistentes y sensibles a fungicidas utilizados en su manejo químico en la zona de Urabá, Colombia, Universidad Nacional de Colombia Sede Medellín.
32. Donini, L. P., Bernardi, E., and Do Nascimento, J. S. (2006) Desenvolvimento in vitro de *Agaricus brasiliensis* em meios suplementados com diferentes farelos, *Pesquisa Agropecuária Brasileira* 41, 995-999.
33. Elad, Y., and Kapat, A. (1999) The role of *Trichoderma harzianum* protease in the biocontrol of *Botrytis cinerea, European Journal of Plant Pathology*, Springer 105, 177-189.
34. Mazurkiewicz-Zapalowicz, K., and Kolodziejczyk, L. (2009) Antagonistic interactions between saprotrophic fungi and geohelminths. 1. Saprotrophic fungi in the biological control of phytopathogenic geohelminths, *Wiadomosci Parazytologiczne* 55, 1-8.
35. Reyes, Y., Martinez, B., and Infante, D. (2008) Evaluation of the antagonistic activity of thirteen *Trichoderma* spp., *Protección Vegetal* 23, 112-117.
36. Viveros, J. (2001) In vitro evaluation of *Trichoderma* and *Gliocladium* antagonism against the symbiotic fungus of the leaf-cutting ant Atta cephalotes, *Mycopathologia* 150, 53-60,
37. Silva, A., Rodrigues, A., Bacci, M., Pagnocca, F. C., and Bueno, O. C. (2006) Susceptibility of the ant-cultivated fungus Leucoagaricus gongylophorus (Agaricales: Basidiomycota) towards microfungi., *Mycopathologia* 162, 115-119.
38. Ceballos, I. C. (2009) Selección de bacterias aeróbicas formadoras de endospora aisladas de la filosfera de cultivares de musa en el Urabá Antioqueño, con potencial antagónico contra *Mycosphaerella fijiensis* Morelet, Universidad Nacional Colombia.
39. Slifkin, M., and Cumbie, R. (1988) Congo red as a fluorochrome for the rapid detection of fungi., *Journal of Clinical Microbiology* 26, 827-830,
40. Riveros, A. S., Giraldo, C. I., and Gamboa, A. (2003) Microbiological control of black leaf streak disease, *Seven* 287-296.
41. Mehrabi, R. Signaling pathways involved in pathogenicity and development of the fungal wheat pathogen *Mycosphaerella graminicola.*
42. Jacome, L. H., Schuh, W., and Stevenson, R. E. (1991) Effect of Temperature and Relative Humidity on Germination and Germ Tube Development of *Mycosphaerella fijiensis* var. *difformis, Phytopathology* 81, 1480-1485.
43. Jacome, L., Lepoivre, P., Marin, D., Ortiz, R., Romero, R., and Escalant, J. V. (2002) *Mycosphaerella* leaf spot diseases of bananas: present status and outlook, *Network* (Jacome, L., Lepoivre, P., Marin, D., Ortiz, R., Romero, R., and Escalant, J. V, Eds.) First edit., pp 71-212, San Jose de Costa Rica.
44. Honma, Y., Nakabayashi, I., Tamaoki, D., Kasahara, H., Ishioka, N., Shimazu, T., Kasahara, H., Yamada, M., Karahara, I., and Kamisaka, S. (2003) Optical microscopy of *Arabidopsis* seedlings fixed in non-fresh FAA using Kennedy Fixation Tubes., *Uchu Seibutsu Kagaku* 17, 307-308.
45. Müller, W. H., Van Aelst, A. C., Humbel, B. M., Van Der Krift, T. P., and Boekhout, T. (2000) Field-emission scanning electron microscopy of the internal cellular organization of fungi., *Scanning* 22, 295-303.
46. Cao, R., Liu, X., Gao, K., Mendgen, K., Kang, Z., Gao, J., Dai, Y., and Wang, X. (2009) Mycoparasitism of endophytic fungi isolated from reed on soilborne phytopathogenic fungi and production of cell wall-degrading enzymes in vitro., *Current Microbiology* 59, 584-592.
47. Beveraggi, A., Mourichon, X., and Salle, G. (1995) Comparative-Study of the First Stages of Infection in Sensitive and Resistant Banana Plants with *Cercospora-Fijiensis* (*Mycosphaerella-Fifiensis*), Responsible for Black Leaf Streak Disease, *Canadian Journal of Botany* 73, 1328-1337.

48. Jing, H.-C., Lovell, D., Gutteridge, R., Jenk, D., Kornyukhin, D., Mitrofanova, O. P., Kema, G. H. J., and Hammond-Kosack, K. E. (2008) Phenotypic and genetic analysis of the *Triticum monococcum-Mycosphaerella graminicola* interaction., *New Phytologist* 179, 1121-1132.

49. Masaphy, S., Levanon, D., Tchelet, R., and Henis, Y. (1987) Scanning Electron Microscope Studies of Interactions between *Agaricus bisporus* (Lang) Sing Hyphae and Bacteria in Casing Soil, *Applied and Environmental Microbiology* 53, 1132-1137.

50, Inbar, J., and Chet, I. (1992) Biomimics of fungal cell-cell recognition by use of lectin-coated nylon fibers., *Journal of Bacteriology* 174, 1055-1059.

51. Zielecka, M., and Wenda, M. (2011) Progress in Organic Coatings Antimicrobial additives for architectural paints and impregnates, *Scanning Electron Microscopy* 72, 193-201.

52. Campos Muñoz, A. (2010) Cell therapy with chondrocytes. Evaluation of cell viability in cultures, *Anales de la Real Academia Nacional de Medicina* 127, 269-281.

53. Semighini, C. P., and Harris, S. D. (2010) Methods to detect apoptotic-like cell death in filamentous fungi., *Methods in Molecular Biology* 638, 269-279.

54. Chung, W. T., Lee, S. H., Kim, J. D., Park, Y. S., Hwang, B., Lee, S. Y., and Lee, H. Y. (2001) Effect of mycelial culture broth of *Ganoderma lucidum* on the growth characteristics of human cell lines., *Journal of bioscience and bioengineering* 92, 550-555.

55. Campos Ziegenbein, F., Hanssen, H.-P., and König, W. A. (2006) Secondary metabolites from *Ganoderma lucidum* and *Spongiporus leucomallellus., Phytochemistry* 67, 202-211.

56. Jong, K.-J., Han, M.-H., Lee, B.-H., Kim, B.-W., Kim, C.-H., Yoon, H.-M., and Choi, Y.-H. (2010) Induction of apoptosis by ethanol extracts of *Ganoderma lucidum* in human gastric carcinoma cells., *Journal of acupuncture and meridian studies*, Korean Pharmacopuncture Institute 3, 24-31.

57. Shimizu, M., and Wariishi, H. (2005) Development of a sample preparation method for fungal proteomics., *FEMS Microbiology Letters* 247, 17-22.

58. Muñoz, K., Bravo, K., Zapata, P., and Londoño, J. (2007) Caracterizacion preliminar del enzima polifenol oxidasa en frutas tropicales: implicaciones en su proceso de industrialización, *Scientia et Technica XIII,* 161-164.

59. Bajorath, J., Hinrichs, W., and Saenger, W. (1988) The enzymatic activity of proteinase K is controlled by calcium., *The Federation of European Biochemical Societies Journal* 176, 441-447.

60, Phansri, K., Sarnthima, R., Thammasirirak, S., Boonchalee, P., and Khammuang, S. (2011) Antibacterial Activity of *Bauhinia* acuminata L. Seed Protein Extract with Low Hemolytic Activity Against Human Erythrocytes, *Chiang Mai Journal of Science* 38, 242-251.

61. Bradford, M. M. (1976) A rapid and sensitive method for the quantitation of microgram quantities of protein utilizing the principle of protein-dye binding., *Analytical biochemistry* 72, 248-54.

62. Rodríguez, A. (2010) Caracterización de proteínas con actividad antifúungica producidas por *Penicillium chrysogenum, Planta*, Universidad de Extremadura.

63. CLSI. (2009) Reference Method for Broth Dilution Antifungal Susceptibility Testing of Filamentous Fungi; Approved Standard—Second Edition, *Clinical and Laboratory Standards Institute* (*CLSI*) 28, 1-35.

64. Espinel-Ingroff, A., Canton, E., and Peman, J. (2009) Updates in antifungal susceptibility testing of filamentous fungi, *Current Fungal Infection Reports* 3, 133-141.

65. Liu, M., Seidel, V., Katerere, D. R., and Gray, A. I. (2007) Colorimetric broth microdilution method for the antifungal screening of plant extracts against yeasts., *Methods* 42, 325-329.

66. Mesa, A. M., Saez, J., Blair Trujillo, S., and Arango, E. (2007) Actividad antiplasmodial de extractos de la planta *Calophyllum lucidum, Scientia et Technica Año* 13, 217-219.

67. Hall, G., and Parshall, S. (2002) Use of the concentration gradient diffusion assay (Etest) for suceptibility testing of anaerobes, fungi, and *Mycobacterium* spp., *Clinical Microbiology Newsletter* 24, 105-109.

The invention claimed is:

1. A procedure for obtaining a protein extract having antifungal activity against *Mycosphaerella fijiensis* comprising the following steps:

a. inoculating *Ganoderma lucidum* in an appropriate culture medium, and culturing under appropriate culture conditions to obtain a *Ganoderma lucidum* biomass;

b. the biomass is obtained under electromagnetic radiation with a wavelength in the range of from 400 to 550 nm; and c. obtaining from said biomass a protein extract having antifungal activity against *Mycosphaerella fijiensis*, the protein extract is obtained by homogenization in a lysis solution comprising a phosphate buffer, Triton X-100, and a hydro-soluble polymer during 5 through 50 homogenization cycles.

2. The procedure according to claim 1 wherein the appropriate culture medium comprises a combination of $NaNO_3$; $KH_2PO_4$; $MgS0_4{\cdot}7H_20$; KCl; barley flour and in a solid, semisolid or liquid matrix in a manual or automated systems.

3. The procedure according to claim 1, wherein the electromagnetic radiation wavelength generates differential, qualitative and quantitative expression of proteins and other bioactive molecules, selected from the group consisting of polysaccharides, triterpenoids, ganoderic acids and fatty acids.

4. The procedure according to claim 1, wherein obtaining the protein extract (step c) comprises the steps of:

a. washing the biomass with the phosphate buffer with pH between 5.0 and 9.0;

b. homogenizing the washed biomass in step (a) with the lysis solution comprising phosphate-buffered saline (PBS), Triton X-100, and the hydro-soluble polymer polyvinylpyrrolidone, for 5 through 50 cycles to obtain a lysate;

c. let stand and filter the lysate obtained in step (b);

d. centrifuge the filtered lysate obtained in step (c), and separate a first supernatant;

e. adding Triton X-100 and polyvinylpyrrolidone to the supernatant obtained in step (d), and homogenize;

f. let stand and centrifuge the homogenate obtained in step (e) to obtain a second supernatant;

g. adding acetone to the second supernatant obtained in step (f) to obtain a precipitate; and h. dissolve the precipitate obtained in step (g) in the phosphate buffer with pH between 5.0 and 9.0 to obtain the protein extract having antifungal activity against *Mycosphaerella Yensis.*

5. The procedure according to claim 4 wherein the homogenization and centrifugation steps are performed at a temperature ranging between 0 and 40° C.

6. The procedure according to claim 4 wherein the homogenization and centrifugation steps are performed in time intervals between 0.1 and 30 minutes.

7. The procedure according to claim 4 wherein the homogenization rate ranges between 5000 and 25000 rpm.

8. The procedure according to claim 4, wherein the acetone in step (g) is added in a 1:1, 2:1, 3:1, 1:3 or 1:2 (v/v) ratio with respect to the supernatant.

* * * * *